United States Patent [19]

Ami

[11] Patent Number: 5,807,562
[45] Date of Patent: Sep. 15, 1998

[54] STICK TYPE COSMETIC

[75] Inventor: Kazuhiro Ami, Gunma, Japan

[73] Assignee: Mitsubishi Pencil Kabushiki Kaisha, Tokyo, Japan

[21] Appl. No.: 892,602

[22] Filed: Jul. 14, 1997

[30] Foreign Application Priority Data

Oct. 22, 1996 [JP] Japan .................................. 8-279649

[51] Int. Cl.$^6$ .............................. A61K 6/00; A61K 7/00; A61K 7/035

[52] U.S. Cl. ............................................ 424/401; 424/69

[58] Field of Search ..................... 424/401, 69; 514/844, 514/951

[56] References Cited

U.S. PATENT DOCUMENTS

| 5,073,364 | 12/1991 | Giezendanner et al. | 424/63 |
| 5,219,560 | 6/1993 | Suzuki et al. | 424/63 |

FOREIGN PATENT DOCUMENTS

| 5313491 | 5/1975 | Japan . |
| 5297399 | 2/1976 | Japan . |
| 5750741 | 7/1976 | Japan . |
| 59-44305 | 3/1984 | Japan . |
| 59-93014 | 5/1984 | Japan . |
| 61-176513 | 8/1986 | Japan . |
| 61-197507 | 9/1986 | Japan . |
| 61-225107 | 10/1986 | Japan . |
| 8188518 | 1/1995 | Japan . |

*Primary Examiner*—Thurman K. Page
*Assistant Examiner*—Sharon Howard
*Attorney, Agent, or Firm*—Darby & Darby

[57] ABSTRACT

The amount of clay such as bentonite, smectite, etc. is limited to a small amount, i.e., 1–10% wt. while the mean diameters of the inorganic extenders and inorganic coloring pigments used are limited to within 0.01 to 50 $\mu$m so that the particle size of the cosmetic when applied is made to fall within the range of 0.01 to 30 $\mu$m. These settings provide a stick type cosmetic imparting a powdery feeling, without granular sensation.

5 Claims, No Drawings

STICK TYPE COSMETIC

BACKGROUND OF THE INVENTION (1) Field of the Invention

The present invention relates to a solid, stick type cosmetic, such as an eyebrow pencil, eyeliner, etc. which is powdery (likely to become powdered), has good use performance and rich in shade and color.

(2) Description of the Prior Art

Conventional solid, stick type cosmetics are obtained by kneading waxy components such as grease, wax, fatty acid, hydrocarbon, etc. as a binder, with coloring matters and extenders to form the compound into a stick shape. However, since they are oily when applied to the skin and the waxy components soften when placed in a high temperature environment, not only do they cause an uncomfortable sensation when applied to the skin but also it becomes difficult to maintain them in a stick shape. Further, it is very likely to give way in use, and if the amount of the waxy components is increased in order to ensure a sufficient breaking resistance, the resultant stick type cosmetic becomes hard, exhibiting poor smoothness and adherence to the skin.

There have been studies on producing stick type cosmetics aiming at achieving a powdery feeling in use without using any waxy components. Examples of proposals include that using a water-soluble glue such as CMC (carboxymethyl cellulose) etc. as a binder (Japanese Patent Application Laid-Open Sho 59 No.44,305) and that using gypsum (Japanese Patent Application Laid-Open Sho 59 No.93,014).

Since in the stick type cosmetics using these binders, the binder will become extremely hard, these cosmetics present an extremely poor, or hard sensation on application to the skin. Further, when these are used to produce a thin shape such as an eyebrow pencil, eyeliner etc., the resultant products are very liable to break off. On the other hand, if the amount of the binder is increased in order to ensure a sufficient breaking resistance, the product can be no longer applied to the skin.

Briefly, the stick type cosmetics which, in order to obtain powdery use performance, use a binder of a water-soluble glue such as CMC or gypsum instead of waxy components, face difficulties in simultaneously providing both a sufficient breaking resistance and a good sensation upon application.

There have been studies on stick type cosmetics which can simultaneously provide both a sufficient breaking resistance and a good sensation upon application without using waxes. In a disclosure (Japanese Patent Application Laid-Open Sho 61 No.176,513 ), the product uses a clay as a binder and is produced by sintering the clay. Another proposal (Japanese Patent Application Laid-Open Sho 61 No.197,507) uses a pore-forming agent to produce a porous sinter.

The invention disclosed in Japanese Patent Application Laid-Open Sho 61 No.176,513 is a stick type cosmetic having a porous skeleton made up of a sintered clay wherein powdery inorganic pigments are dispersed. In this disclosure, reference is made to the porous material 'as the porosity is increased, the touch and application performance during use tends to become better, conversely as the porosity is reduced, the strength becomes higher'. Resultantly, this publication proposed a sinter having a porosity of about 50% to 90%.

To sum up, the sinter made up of clay provides a sufficient breaking resistance but is too hard to be applied to the skin. On the other hand, the sinter made up of porous material can provide a stick type cosmetic which simultaneously provides both a sufficient breaking resistance and a good sensation upon application.

In order to meet the requirements of both the good sensation upon application and a sufficient breaking resistance, the adjustment of the porosity is an unavoidable factor. However, mere adjustment of the temperature during the sintering process and the ratio of the clay to the powdery pigment as written in the publication faces crucial difficulties in producing a sinter having the preferred porosity of about 50% to 90% as specified in the disclosure. In order to achieve a porosity falling within such a range, it is necessary to create pores by burning excipients and molding assisting agents, made up of various kinds of resins added for molding, in an oxygen atmosphere to remove them during sintering or by depolymerizing them in an inert atmosphere to remove them, or it is necessary to intentionally create pores by using a pore forming agent as disclosed in the above application, i.e. Japanese Patent Application Laid-Open Sho 61 No.197,507.

However, in the removing method by burning resins added for molding during sintering in an oxygen atmosphere, the color pigments are also oxidized during the sintering process. Therefore, when easily oxidized coloring pigments such as iron black, carbon black and titanium black are used as black pigments, the pigments are tarnished or discolored so that it becomes impossible to produce the desired shade and color.

In the method for removing the additives by depolymerizing them in an inert atmosphere, the resins etc. become carbides remaining within the stick type cosmetic, being very difficult to remove completely. Consequently, the resultant stick type cosmetic becomes dark, resulting in failure to produce the desired shade and color. Even when a resin, such as polymethyl methacrylate or the like, which is relatively unlikely to leave behind carbides, is used, a small amount of carbides still remains within the stick type cosmetic. To remove them completely, it is accordingly necessary to use a method of sintering them under an oxidizing atmosphere. Further, these carbides not only become an obstacle against producing the desired shade and color but also produce various abnormal byproducts. Moreover, when polymethyl methacrylate are depolarized, monomers arising during this reaction is extremely high in toxicity, giving rise to a problem of safety in cosmetics.

In the method of forming pores by using a pore-forming agent and removing the pore-forming agent with a chemical agent after sintering, disclosed in Japanese Patent Application Sho 61 No.197,507, there is no concern about remanent carbides as stated above. It is however very difficult to remove the pore-forming agent from a stick type cosmetic by chemical treatment. In practice, when the pore-forming agent is removed in a manner such as this, since the pore-forming agent should be eluted from the stick type cosmetic using a chemical agent the stick type cosmetic becomes deformed so that it is almost impossible to completely remove the pore-forming agent whilst maintaining its shape.

Resultantly, some of the pore-forming agent will remain as impurities in the stick type cosmetic. This not only causes failure to form a sufficient number of pores but gives rise to a problem of safety in the cosmetic.

As methods for obtaining a sinter of inorganic pigments rich in shade and color, various proposals have been disclosed: Japanese Patent Application Laid-Open Sho 52 No.97,399, Japanese Patent Publication Sho 53 No.13,491 and Japanese Patent Publication Sho 57 No.50,741. All these are not for stick type cosmetics but are for pigments or powdery cosmetics. Actually, these methods can provide cosmetic powders rich in shade and color, but can not be applied to form the powder into a stick shape and keep its shape. Briefly, it is impossible for these methods to yield a solid, stick type cosmetic.

A method for creating solid stick type cosmetics with a variety of shades and colors was proposed in Japanese Patent Application Laid-Open Sho 61 No.225,107. In this method, color is changed by a heating process. Therefore, if two or more kinds of coloring agents are used simultaneously, each coloring matter uniquely changes: for example, if iron black and red iron oxide are used to represent brown color, iron black and red iron oxide change independently under the heat treatment, thus resulting in failure to present the desired brown. Actually, in the method of changing colors by a heat process, variation in shade and color obtained is limited, thus it is very difficult to obtain various kinds of shades and colors required for stick type cosmetics.

SUMMARY OF THE INVENTION

The inventors hereof have proposed a stick type cosmetic by Japanese Patent Application Laid-Open Hei 8 No.188,518, which consists essentially, of at least one kind selected from a group of bentonite, smectite, montmorillonite, beidellite, nontronite, hectorite and saponite, in an amount by weight of 1–10%, an inorganic extender and an inorganic coloring pigment, wherein these materials are sintered at a temperature of 300° C. to 1,000° C., to produce a molded composition of an inorganic powder free from carbides left and water, and then after drying, the molding is heated at a temperature of 300° C. to 1,000° C. to produce a stick type cosmetic.

The present invention relates to improvement of Japanese Patent Application Laid-Open Hei 8 No.188,518.

In general, stick type cosmetics using clay as a binder are liable to impart a granular sensation upon application, so that in the Japanese Patent Application Laid-Open Hei 8 No.188, 518, the clay is limited to a small amount, i.e. falling within the range of 1 to 10% wt. in order to prevent this. This invention is to provide a stick type cosmetic further improved in its granular-free characteristic.

The present inventors have done extensive study to achieve the above object, and found that in the stick type cosmetic disclosed in Japanese Patent Application Laid-Open Hei 8 No.188,518, by limiting both the mean particle sizes of the inorganic extender and inorganic coloring pigment to be used as starting materials to within 0.01–50 $\mu$m, it became possible to limit the particle size after abrasion and pulverization of the stick type cosmetic within the range of 0.01 to 30 $\mu$m, and hence obtain a stick type cosmetic free from granular feeling. Thus, the present invention has been achieved.

Actually, in accordance with the first aspect of the invention, a stick type cosmetic consisting, essentially, of at least one kind selected from a group of bentonite, smectite, montmorillonite, beidellite, nontronite, hectorite and saponite, in an amount by weight of 1–10%, an inorganic extender and an inorganic coloring pigment, both having a mean particle size of 0.01 $\mu$m to 50 $\mu$m, is processed in such a manner that these materials are sintered at a temperature of 300° C. to 1,000° C., to produce a bar-shaped molded composition of inorganic powder having pores and free from carbides, and then the molding is heated at a temperature of 300° C. to 1,000° C. so that when applied, the particle size falls within the range of 0.01–30 $\mu$m.

In accordance with the second aspect of the invention, a stick type cosmetic having the above first feature has a porosity of 5–45%.

In accordance with the third and fourth aspects of the invention, a stick type cosmetic having the above first or second feature is characterized in that the pores are impregnated with a grease or wax containing at lease one kind selected from a group of silicone oil, hydrocarbons, ester liquid oil, ester paste and a surfactant.

DESCRIPTION OF THE PREFERRED EMBODIMENTS

Reason for limiting conditions in this invention will be described first. In this invention, at least one kind of clay selected from a group of bentonite, smectite, montmorillonite, beidellite, nontronite, hectorite and saponite is used in the amount of 1 to 10% wt. These materials will not leave carbides at all after a sintering process at a temperature of 300° to 1,000° C.

Examples of inorganic extenders include kaolin, calcium carbonate, mica, boron nitride, spherical silica, talc etc. having a mean particle size of 0.01 to 50 $\mu$m. These also will not leave carbides at all after a sintering process at a temperature of 300° to 1,000° C.

Examples of the inorganic coloring pigments include titanium oxide, iron black, carbon black, chromium oxide, ultramarine, red iron oxide, pigments made up of composite oxides, etc., with a mean particle size of 0.01 to 50 $\mu$m. These also will neither change in color nor produce carbides under a sintering process of 300° C. to 700° C. if in an inert atmosphere. In view of avoiding change of the pigments in color, the sintering temperature is preferably 700° C. or below.

In order to knead these inorganic extenders and inorganic coloring pigments, water, volatile solvents, volatile oils or combination of them can be used, but a preferred selection of volatile solvents and volatile oils etc. is that which will evaporate completely without any residue, from the sinter after sintering.

In this invention the inorganic extenders and inorganic coloring pigments which should be used are those having a mean particle size of 0.01 to 50 $\mu$m so that the resultant stick type cosmetic presents a particle size of 0.01 to 30 $\mu$m when it is applied (abraded and crushed). These setting of the materials will not cause any granular sensation.

If the particle size when applied is smaller than 0.01 $\mu$m, a satisfactorily powdery feeling is not obtained (or, the cosmetic is over crushed), and the cosmetic is too hard to be applied smoothly. If the particle size is greater than 30 $\mu$m, the cosmetic not only gives a granular sensation upon application but also is lowered in its adherence to the skin.

The temperature during sintering is set within 300° C. to 1,000° C., preferably 400° C. to 800° C., and more preferably 500° C. to 700° C.

In the stick type cosmetic of the invention, pores should be created at a porosity of 5 to 45%, after molding and sintering. If the porosity is less than 5%, the stick type cosmetic becomes hard so that it can not provide a satisfactory powdery feeling and good sensation upon application. In contrast, if the porosity is greater 45%, the breaking resistance becomes low because the clay component is constrained at between 1 to 10% wt. The porosity preferably falls within the range of 15 to 30%.

In the stick type cosmetic of the invention, no waxes are used as the binder. But, in order to improve the feeling upon application to the skin, oils or waxes such as silicone oil, hydrocarbons etc. are allowed to be used, or rather preferably used, to impregnate the pores in view of enhancing the feeling upon application.

Next, the embodiment of the invention will be described illustratively together with comparative examples in order to detail the effect of the invention, but the present invention should not be limited to these examples. Here, 'part' shows a part by weight'.

(EXAMPLE 1)

| | |
|---|---|
| saponite | 7 parts |
| kaolin (with 5 μm in mean diameter) | 26 parts |
| calcium carbonate (with 10 μm in mean diameter) | 25 parts |
| talc (with 4 μm in mean diameter) | 25 parts |
| iron black (with 0.3 μm in mean diameter) | 5 parts |
| titanium oxide (with 0.2 μm in mean diameter) | 12 parts |

These materials were blended in a mixer to be uniform and kneaded by a kneader and then were formed into a rod of 2.5 mm in diameter by an extrusion molding machine. The molding was dried for 5 hours at 150° C. so as to expel moisture completely. The dried rods were placed in a ceramic container and then were heated in an electric furnace under an inert atmosphere for eight hours at 650° C. After cooling, gray rods were obtained which, when applied to the skin, presented the particle size shown in Table 1 and gave powdery and satisfactory sensation upon application. The rod was immersed in silicone oil for three hours. Then, it was subjected to a centrifugal separator so that extra silicon oil was removed therefrom.

Then this rod was cut into sticks of 90 mm long. Here, the porosity of the rod before impregnation of silicon oil was 25%.

(N.B.) the porosity was measured by a substitution method (at 20° C.). More specifically, the porosity was calculated by the following formula:

$$porosity = 100 \times (W' - W) / \rho V \, (\%)$$

where V is the volume of the rod, W the weight of the rod, W' the weight of the rod after being immersed in water, ρ the density of water.

(EXAMPLE 2)

| | |
|---|---|
| bentonite | 5 parts |
| kaolin (with 15 μm in mean diameter) | 40 parts |
| mica (with 5 μm in mean diameter) | 25 parts |
| carbon black (with 0.05 μm in mean diameter) | 10 parts |
| red iron oxide (with 0.3 μm in mean diameter) | 20 parts |

These compounds were processed in the same manner as in example 1, and reddish brown rods having a porosity of 20% were obtained. This presented the particle size shown in Table 1, when applied to the skin.

(EXAMPLE 3)

| | |
|---|---|
| smectite | 5 parts |
| kaolin (with 15 μm mean diameter) | 55 parts |
| talc (with 4 μm in mean diameter) | 20 parts |
| ultramarine (with 0.1 μm in mean diameter) | 20 parts |

These compounds were processed in the same manner as in example 1, and blue rods having a porosity of 25% were obtained. This presented the particle size shown in Table 1, when applied to the skin.

(Comparative Example 1)

An example of a conventional stick type cosmetic mainly composed of waxes

| | |
|---|---|
| beeswax | 20 parts |
| ozokerite | 10 parts |
| micro crystalline wax | 10 parts |
| carnauba wax | 8 parts |
| Vaseline | 7 parts |
| lanolin | 5 parts |
| liquid paraffin | 7 parts |
| isopropyl myristate | 4 parts |

These materials were dissolved and 10 parts of black iron and 19 parts of red iron oxide were added to the solution. Then, after agitation and dispersion, this was kneaded by a mixer and cooled to room temperature. The resultant was formed by an extrusion molding machine into a reddish brown rod of 2.5 mm in diameter, which in turn was cut into sticks of 40 mm long.

(Comparative Example 2)

An example using bentonite in an

| | |
|---|---|
| bentonite | 15 parts |
| kaolin (with 15 μm in mean diameter) | 50 parts |
| carbon black (with 10 μm in mean diameter) | 10 parts |
| red iron oxide (with 0.3 μm in mean diameter) | 20 parts |

These compounds were processed in the same manner as in example 1, and reddish brown rods were obtained. This presented the particle size shown in Table 1, when applied to the skin.

(Comparative Example 3)

| | |
|---|---|
| saponite | 7 parts |
| kaolin (with 30 μm in mean diameter) | 50 parts |
| talc (with 10 μm in mean diameter) | 25 parts |
| iron black (with 0.3 μm in mean diameter) | 5 parts |
| titanium oxide (with 0.2 μm in mean diameter) | 13 parts |

These compounds were processed in the same manner as in example 1, and gray rods were obtained. This presented the particle size shown in Table 1, when applied to the skin.

For the sticks obtained in examples 1–3 and comparative examples 1–3, breaking resistance, sensation upon application to the skin, the particle size at application were evaluated by the following methods;

(Breaking resistance)

A rod having a diameter d (mm) was placed between two fulcrums (with a span of 22 mm), and a load was imposed at the middle point of the rod at a rate of 10 mm per minute at 30° C. From the load P (gf) with which the rod was broken, the breaking resistance was calculated using the following formula:

$$\text{Breaking resistance} = 8 \times P \times 22 / \pi d^3 \, (gf/mm^2)$$

In this experiment, the tip of the point by which the load was applied as well as the tips of the fulcrums had a hemispherical shape of about 0.2 mm in radius (R).

(Sensation upon application to the skin)

Concerning the use feeling when the stick type cosmetics were applied to the skin, an organoleptic test was implemented with a panel made up of 20 females, based on the following four levels of evaluation, and the mean was shown in Table 1.

⊚:good, ○:acceptable, △:granular ▽:greasy (Particle size upon application)

At a 23° C., 65% RH atmosphere, each stick was tested on a pencil writing test machine (made by SEIKI KOGYO) onto high-quality paper (made by SUGIURA SHIKO) with a writing load of 100 g, a writing speed of 50 mm/sec in a writing distance of 2.62 m. The particles applied on the written surface was observed by an electron microscope to measure the particle size.

TABLE 1

|  | Breaking resistance (gf/mm$^2$) | Sensation upon application to the skin | Particle size (μm) at application |
| --- | --- | --- | --- |
| Ex. 1 | 720 | ○ | 10 |
| 2 | 540 | ◉ | 5 |
| 3 | 610 | ◉ | 6 |
| CEx. 1 | 160 | ▽ | — |
| CEx. 2 | 1070 | △ | 20 |
| CEx. 3 | 690 | △ | 50 |

From the result in Table 1, each product from the examples of the invention presents good sensation upon application to the skin. In contrast, the product obtained in comparative example 1 has a breaking resistance which is lower than half of those in the examples, and presents greasy feeling upon application to the skin.

The product obtained in comparative example 2 has a particle size of 30 μm or below during application, but gives granular feeling due to an excessive amount of clay.

The product obtained in comparative example 3 has a particle size of more 30 μm during application, presenting granular feeling upon application.

Thus, the stick type cosmetic of the invention is excellent in maintaining its shape, gives a powdery sensation, and hence is advantageous for solid, stick type cosmetics.

In accordance with the invention, the amount of clay such as bentonite, smectite, etc. is limited to 1–10% wt. while the mean diameters of the inorganic extenders and inorganic coloring pigments are limited to within 0.01 to 50 μm. These materials are sintered at a temperature of 300° C. to 1,000° C., to be formed into a bar-shaped molding. When the sintering is effected within the above temperature range, the particle size upon application to the skin falls within the range of 0.01–30 μm. These settings provide a stick type cosmetic imparting a powdery feeling, without any granular sensation.

What is claimed is:

1. A solid stick cosmetic consisting essentially of at least one component selected from the group consisting of bentonite, smectite, montmorillonite, beidellite, nontronite, hectorite, and saponite, wherein said component is present in an amount by weight of 1–10%, an inorganic extender and an inorganic coloring pigment, both having a mean particle size of 0.01 mm to 50 mm, wherein the at least one component, inorganic extender, and inorganic coloring pigment are sintered at a temperature of 300° C. to 1,000° C., to produce a bar-shaped molding composition of inorganic powder having pores and being free from carbides, wherein said molding composition is heated at a temperature of 300° C. to 1,000° C. so that upon application, the particle size falls within a range of 0.01–30 mm.

2. A solid stick cosmetic according to claim 1, wherein the porosity is 5–45%.

3. A solid stick cosmetic according to claim 1, wherein the pores are impregnated with a grease or wax containing at least one kind selected from a group of silicone oil, hydrocarbons, ester liquid oil, ester paste and a surfactant.

4. A solid stick cosmetic according to claim 2, wherein the pores are impregnated with a grease or wax containing at lease one kind selected from a group of silicone oil, hydrocarbons, ester liquid oil, ester paste and a surfactant.

5. A solid stick cosmetic according to claim 1, wherein said cosmetic is selected from the group consisting of an eyebrow pencil and an eyeliner.

* * * * *